(12) United States Patent
Baxi et al.

(10) Patent No.: US 9,936,919 B2
(45) Date of Patent: Apr. 10, 2018

(54) DEVICES, SYSTEMS, AND METHODS FOR DETERMINING HEART RATE OF A SUBJECT FROM NOISY ELECTROCARDIOGRAM DATA

(71) Applicant: Intel Corporation, Santa Clara, CA (US)

(72) Inventors: Amit Baxi, Thane (IN); Mayank Garg, New Delhi (IN)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 14/866,764

(22) Filed: Sep. 25, 2015

(65) Prior Publication Data

US 2017/0086752 A1 Mar. 30, 2017

(51) Int. Cl.
| | |
|---|---|
| *A61B 5/00* | (2006.01) |
| *A61B 5/0245* | (2006.01) |
| *A61B 5/0456* | (2006.01) |
| *A61B 5/0408* | (2006.01) |
| *A61B 5/04* | (2006.01) |

(52) U.S. Cl.
CPC .......... *A61B 5/7203* (2013.01); *A61B 5/0245* (2013.01); *A61B 5/0408* (2013.01); *A61B 5/04017* (2013.01); *A61B 5/0456* (2013.01); *A61B 5/726* (2013.01)

(58) Field of Classification Search
CPC ..... A61B 5/024; A61B 5/0456; A61B 5/0245; A61B 5/04017; A61B 5/72-5/7264
See application file for complete search history.

(56) References Cited

U.S. PATENT DOCUMENTS

| | | | |
|---|---|---|---|
| 5,309,917 A * | 5/1994 | Wang ................. | A61B 5/04012 600/508 |
| 8,632,465 B1 * | 1/2014 | Brockway .......... | H03H 17/0248 600/300 |
| 2009/0259271 A1 * | 10/2009 | Allavatam ........... | A61B 5/0452 607/25 |
| 2010/0074482 A1 | 3/2010 | Toth et al. | |
| 2012/0130263 A1 * | 5/2012 | Pretorius .............. | A61B 5/0245 600/509 |
| 2014/0005563 A1 | 1/2014 | Ramanathan et al. | |
| 2014/0005988 A1 | 1/2014 | Brockway | |
| 2014/0052007 A1 * | 2/2014 | Mcgregor ............ | A61B 5/0205 600/484 |
| 2014/0128758 A1 | 5/2014 | Galloway et al. | |
| 2015/0273313 A1 * | 10/2015 | Chen ..................... | A61B 5/024 700/91 |

FOREIGN PATENT DOCUMENTS

WO WO 1997/017015 A1 5/1997

OTHER PUBLICATIONS

International Search Report for PCT application No. PCT/US2016/050424; dated Dec. 12, 2016, 11 pages.

* cited by examiner

*Primary Examiner* — Scott Getzow
(74) *Attorney, Agent, or Firm* — Thorpe North & Western, LLP; David W. Osborne (57) ABSTRACT

Devices, systems, and associated methods for determining heart rate (HR) of a subject from noisy Electrocardiogram (ECG) data are disclosed and described.

30 Claims, 6 Drawing Sheets

DEVICES, SYSTEMS, AND METHODS FOR DETERMINING HEART RATE OF A SUBJECT FROM NOISY ELECTROCARDIOGRAM DATA

BACKGROUND

The popularity of health monitoring devices has grown in recent years, from machines in stores and pharmacies that measure blood pressure, to dedicated wearables, and smart phone, smart watch, and tablet apps that monitor activity, food intake, and more. Such devices often require that a user purposefully perform a test or enter some form of data to facilitate monitoring activity.

DESCRIPTION OF EMBODIMENTS

Although the following detailed description contains many specifics for the purpose of illustration, a person of ordinary skill in the art will appreciate that many variations and alterations to the following details can be made and are considered to be included herein.

Accordingly, the following embodiments are set forth without any loss of generality to, and without imposing limitations upon, any claims set forth. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which this disclosure belongs.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term in the specification, like "comprising" or "including," it is understood that direct support should be afforded also to "consisting essentially of" language as well as "consisting of" language as if stated explicitly and vice versa.

"The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein.

As used herein, "enhanced," "improved," "performance-enhanced," "upgraded," and the like, when used in connection with the description of a device or process, refers to a characteristic of the device or process that provides measurably better form or function as compared to previously known devices or processes. This applies both to the form and function of individual components in a device or process, as well as to such devices or processes as a whole.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of"

an ingredient or element may still actually contain such item as long as there is no measurable effect thereof.

As used herein, the term "about" is used to provide flexibility to a numerical range endpoint by providing that a given value may be "a little above" or "a little below" the endpoint. However, it is to be understood that even when the term "about" is used in the present specification in connection with a specific numerical value, that support for the exact numerical value recited apart from the "about" terminology is also provided.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.3, 3, 3.8, 4, 4.6, 5, and 5.1 individually.

This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

EXAMPLE EMBODIMENTS

An initial overview of technology embodiments is provided below and specific technology embodiments are then described in further detail. This initial summary is intended to aid readers in understanding the technology more quickly, but is not intended to identify key or essential technological features, nor is it intended to limit the scope of the claimed subject matter.

For many individuals, it can be desirable to perform periodic or continuous health monitoring, either due to an existing medical condition, a potential medical condition, or a desire to maintain good physical fitness. One physiological parameter that can be beneficial to monitor is heart rate (HR). An Electrocardiograph (ECG) recording is an effective method of measuring many heart-related physiological effects, including HR. An ECG is a physiological signal that can be measured through electrodes coupled to the chest of a subject, as well as electrodes associated with wearable devices, mobile computing devices, smart phones, and even exercise equipment. ECG recordings can measure electrical impulses generated by polarization and depolarization events in cardiac tissue of the heart, and translate these electrical impulses into an ECG signal, or ECG data. The ECG signal can provide a measure of the rate and regularity of heartbeats, among other things.

Figure 1A:
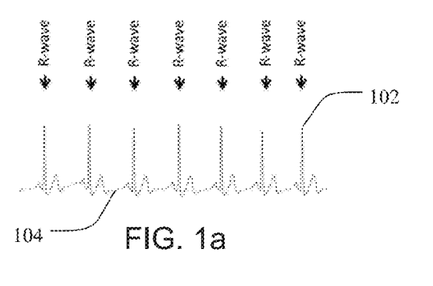
FIG. 1a is a graphical representation of ECG data in accordance with an invention embodiment.
Figure 1B:
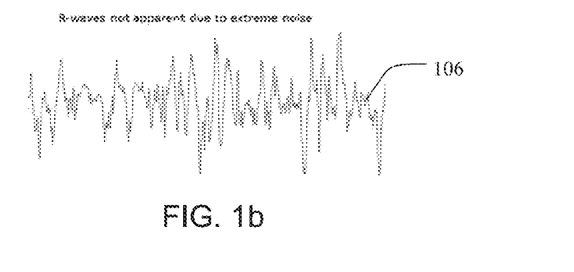
FIG. 1b is a graphical representation of ECG data in accordance with an invention embodiment.

Two ways in which ECG signals can be recorded are intentionally and opportunistically. In some intentional ECG recordings, the subject can be positioned in a prone or sitting position where electrodes are coupled directly to the chest. In other intentional ECG recordings, the user intentionally grasps or otherwise touches electrodes with little movement. The quality of ECG signals obtained by intentional ECG sensing is generally good, as is shown in FIG. 1a for example. The R-waves (or R-peaks) 102 are easily distinguishable from the baseline noise 104, and as such the peaks can readily be extracted by a process such as windowing or thresholding, to directly measure HR. In some cases, however, intentional ECG recordings can be very noisy for various reasons. Substances on the skin of the subject can interfere with the recording, subject movement during recording, poor electrode connections, interference from nearby electronic equipment, and the like. Additionally, opportunistic recordings are generally very noisy as well. Opportunistic recordings can refer to various situations where ECG signals are being recorded, such as a subject unintentionally touching electrodes, a subject using an object or device (such as a laptop, for example) having ECG electrodes, wearable sensors that intermittently contact the skin of a subject, and the like. An example of an opportunistic ECG recording is shown in FIG. 1b, where induced noise 106 can be several times the magnitude of ECG signal, thus obscuring it completely. In some cases noise can be introduced due to changes in contact surface area between the skin and the electrode, due to changes in contact pressure, and the like. For such ECG data, conventional signal processing techniques are ineffective at extracting the R-peak data from the baseline noise.

As can be appreciated from the ECG recording in FIG. 1b, estimating HR from either opportunistically recorded ECG, or from intentionally recorded ECG having a high degree of noise, can be extremely challenging. Such recordings can be very useful, however, because they can facilitate the unobtrusive, and in some cases continuous, monitoring of HR. As an added difficulty, the frequency bands of noise and ECG signal overlap, thus further complicating accurate HR estimations from noisy ECG signals. Furthermore, opportunistic HR monitoring can open the door to many applications, such as, for example, assessing mental stress and stress monitoring, emotion classification, assessing cardiac fitness, and the like. Erroneous HR estimations due to noisy ECG recordings, however, can lead to erroneous estimations of a subject's state.

Invention embodiments present novel devices, systems, and methods for accurately extracting HR information from noisy ECG signals, thereby improving numerous aspects of healthcare and personal health management, including paving the way for various opportunistic bio-sensing applications on mainstream client computing devices. These devices, systems, and methods can accurately extract HR even from extremely noisy opportunistically sensed ECG signals such as is shown in FIG. 1b. Traditional HR estimation algorithms often use high-pass filters or wavelet filtering to stabilize the ECG baseline, after which the HR data is extracted using threshold-based peak detection in the time domain, or by time domain analysis. The beat-to-beat HR is then calculated using the extracted peak time-intervals. Alternatively, some traditional algorithms use spectral analysis in the frequency domain (such as FFT and wavelets) to determine spectral energy distribution, and then apply thresholds to detect the frequency of the R-waves or R-peaks. Due to the often severe contamination by noise in many opportunistic sensing scenarios, these algorithms are generally ineffective.

Figure 2:
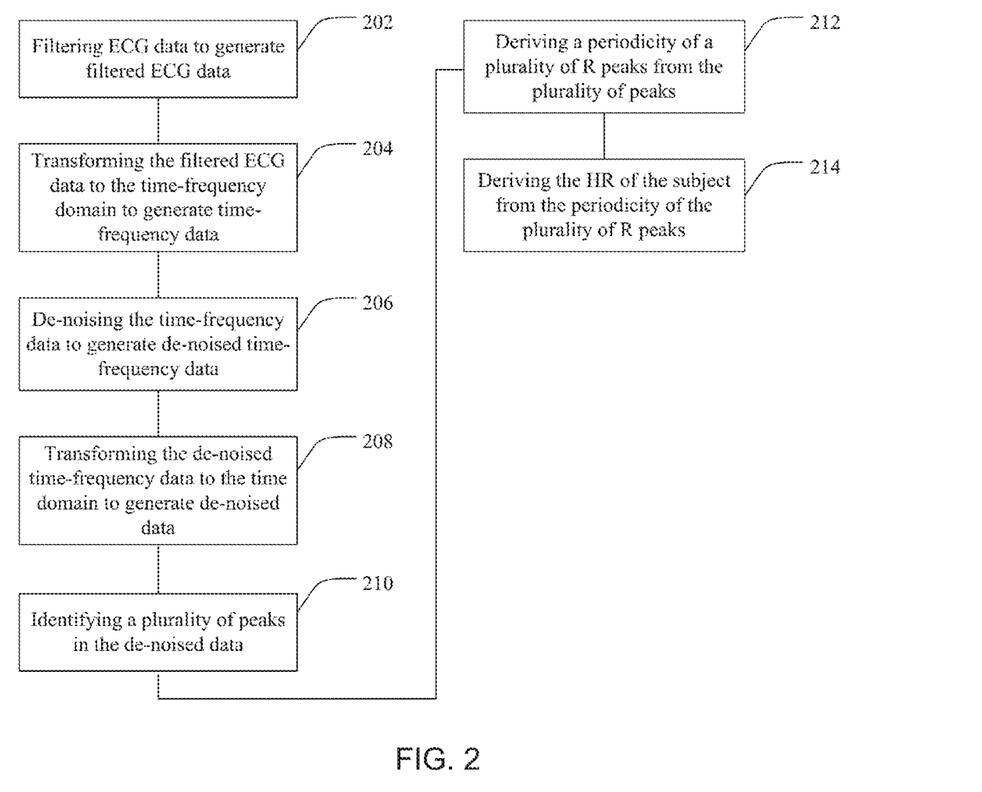
FIG. 2 is a depiction of a method for determining HR of a subject from noisy ECG data in accordance with an invention embodiment.

The presently disclosed approach applies novel signal processing methodology in both the time and frequency domains to systematically enhance and extract the rhythm or periodicity in the underlying noisy ECG signal, and uses this periodicity to calculate HR. It is noted that this methodology can be applied to both intentional and opportunistic ECG recording, both of which are within the present scope. In one example, as is shown in FIG. 2, a method for determining HR of a subject from noisy ECG data is provided. The method can include 202 filtering ECG data to generate filtered ECG data, 204 transforming the filtered ECG data to the time-frequency domain to generate time-frequency data, 206 de-noising the time-frequency data to generate de-noised time-frequency data, 208 transforming the de-noised time-frequency data to the time domain to generate de-noised data, 210 identifying a plurality of peaks in the de-noised data, 212 deriving a periodicity of a plurality of R peaks from the plurality of peaks, and 214 deriving the HR of the subject from the periodicity of the plurality of R peaks.

Figure 3A:
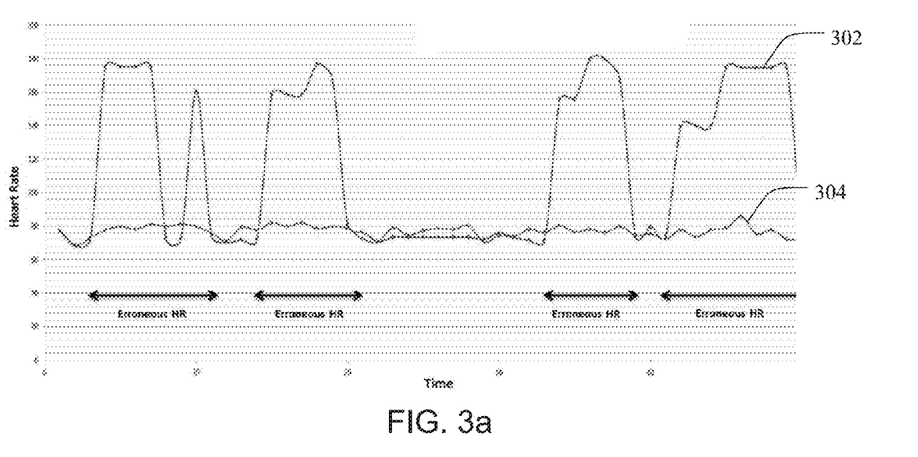
FIG. 3a is a graphical representation of HR data in accordance with an invention embodiment.
Figure 3B:
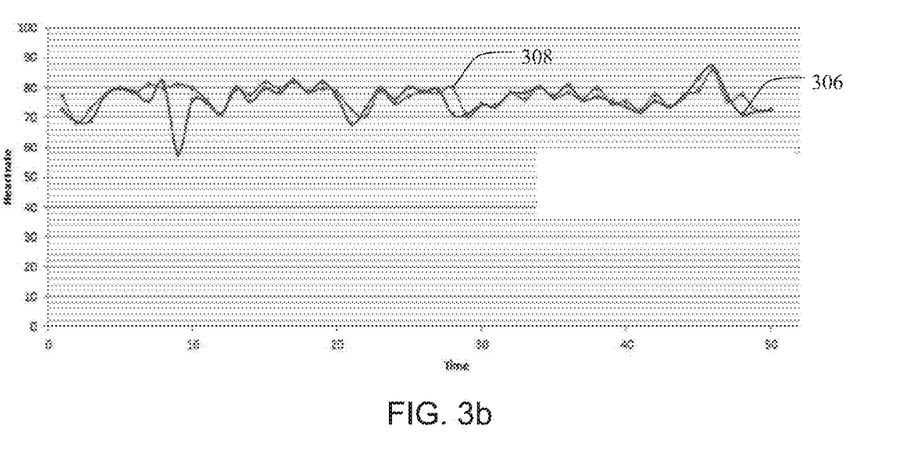
FIG. 3b is a graphical representation of HR data in accordance with an invention embodiment.

As has been described, the presently disclosed approach significantly increases the accuracy of HR measurements from noisy ECG data as compared to traditional approaches, and additionally can extract HR effectively from ECG data that cannot be processed using traditional approaches due the very high levels of noise. FIGS. 3a-b show an example comparison of HR extraction from noisy ECG data using a traditional approach (FIG. 3a) and an approach according to an invention embodiment (FIG. 3b). The ECG data was opportunistically acquired from electrodes placed on the palm rest of a laptop computer. As movement of the hands naturally occurs during typing, the resulting ECG data is noisy. As an individual is typing, ECG data is opportunistically recorded whenever both palms simultaneously touch the electrodes on both sides of the laptop. In addition to the opportunistic recording, adhesive electrodes were attached to the chest of the test subject in order to record a stable ECG and HR for reference. FIG. 3a shows the performance of a traditional HR extraction technique on the opportunistic ECG data 302 compared to the HR reference 304. During periods of typing, noted by the upward spikes in HR, the performance of the traditional HR extraction technique was very inaccurate, measuring erroneous HRs of up to 180 b/m when the HR control shows the actual HR of the subject to be around 80 b/m.

FIG. 3b shows the performance of the presently disclosed approach, using the same electrode setup on the laptop, and adhesive electrodes attached to the subject's chest to record a stable ECG and HR for reference. In sharp contrast to the traditional approach, the opportunistic ECG data 306 closely tracks the HR reference 308, even during periods of aggressive keyboard use. The mean error of the opportunistic ECG data 306 against the control 308 is <3%.

ECG data can initially be filtered to remove or otherwise minimize noise associated with 50/60 Hz line noise, muscle tremor noise, baseline DC drift, motion noise, and the like, which is inherent in ECG systems. In one example, a low pass filter can be applied to the ECG data in order to remove the 50/60 Hz line nose, muscle tremor, and any other higher frequency noise. In another example, a high pass filter can be applied to the ECG data in order to remove the baseline DC drift, the motion noise, or any other lower frequency noise. In yet another example, both a low pass filter and a high pass filter can be applied to the ECG data to achieve noise filtration of both higher and lower frequency noise. Additionally, a band pass filter can be utilized to the same effect as a combined low pass and high pass filter.

Any type of low pass filter can be utilized to filter the ECG data, and various low pass filter characteristics and/or parameters can be used, depending on the nature of the data, the desired filtering characteristics, the opportunistic data gathering system, and the like. In one embodiment, a low pass filter is applied and can be tuned to pass the R-peak data and filter noise having energy above the R-peak data energy. Any given frequency range of noise can be allowed to pass through the filter provided HR can still effectively be measured. In one example, however, the low pass filter has a cutoff frequency of 30 Hz or less. In another example, the low pass filter has a cutoff frequency of 25 Hz or less. In yet another example, the low pass filter has a cutoff frequency of 22 Hz or less. Furthermore, the sharpness of the low pass filter can be of any sharpness tolerable by the system, or in other words, any sharpness that still allows HR to be effectively measured or estimated. In one specific example, however, the low pass filter is of order 2 or more. In another example, the low pass filter is of order 5 or more. In yet another example, the low pass filter is of order 8 or more.

Similarly, with respect to high pass filters, in one example a cutoff frequency can be 2 Hz or more. In another example, the high pass filter has a cutoff frequency of 7 Hz or more. In yet another example, the high pass filter has a cutoff frequency of 14 Hz or more. As with low pass filters, the sharpness of the high pass filter can be of any sharpness tolerable by the system, and which still allows HR to be effectively measured or estimated. In one specific example, however, the high pass filter is of order 2 or more. In another example, the high pass filter is of order 5 or more. In yet another example, the high pass filter is of order 8 or more.

As described, the ECG data can be filtered with a band pass filter. Similar to the low and high pass filters, in one example, the band pass filter has a lower cutoff frequency of 2 Hz or more and an upper cutoff frequency of 30 Hz or less. In another example, the band pass filter has a lower cutoff frequency of 7 Hz or more and an upper cutoff frequency of 25 Hz or less. In yet another example, the band pass filter has a lower cutoff frequency of 14 Hz or more and an upper cutoff frequency of 22 Hz or less. As with low and high pass filters, the sharpness of the band pass filter can be of any sharpness tolerable by the system, and which still allows HR to be effectively measured or estimated. In one example, the band pass filter is of order 2 or more. In another example, the band pass filter is of order 5 or more. In yet another example, the band pass filter is of order 8 or more. Additionally, in some cases it filtering the ECG data can include filtering with a low pass filter and a band pass filter, or filtering with a bandpass filter and a high pass filter.

Numerous filters and filter types can be utilized to filter the ECG data. Those of ordinary skill in the art will readily note, once in possession of the present disclosure, a wide variety of filter types, filter combinations, techniques, and the like, that can be utilized to accomplish various invention embodiments, all of which are considered to be within the present scope. A filter can be hardware-based, software-based, can include elements of both hardware and software, and the like. In one example, a filter can include an infinite impulse response (IIR) filter. In another example, a filter can include a finite impulse response (FIR) filter. Non-limiting examples of various filter types includes Savitzky-Golay filters, Elliptic filters, Chebyshev filters, Butterworth filters, Bessel filters, and the like, including combinations thereof. These filters and others are individually well-known to those of ordinary skill in the art. In one specific example, the filter is a Savitzky-Golay filter. In another specific example, the filter is a Butterworth filter.

Figure 4:
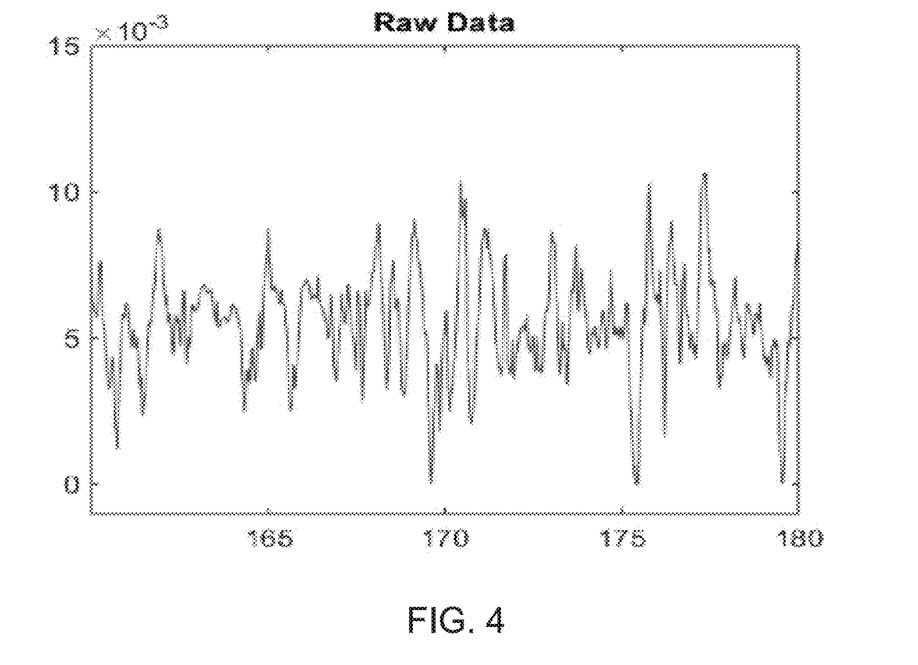
FIG. 4 is a graphical representation of raw ECG data in accordance with an invention embodiment.

Additionally, in some cases the ECG data can be processed in discrete chunks, packets, or segments. For each chunk, packet, or segment of ECG data, HR is estimated. Data chunks, packets, or segments or any length or size of can be used, and can be varied depending on the condition of the data, the processing and system specifications, and the like. Since motion-noise during opportunistic ECG recording can occupy a broad frequency spectrum, it overlaps with the ECG signal spectrum and limits the effectiveness of traditional filters. Processing ECG data in discrete chunks mitigates at least some of the randomness of the noise in the signal, because over the duration of the chunk there is relatively more periodicity information present to make reasonable inferences about HR. A sample ECG chunk is shown in FIG. 4, where even visually it is difficult if not impossible to identify ECG signal from noise.

In one specific example, a Savitzky-Golay filter can be applied to the ECG data to smooth the data and remove the higher frequencies, such as the 50/60 Hz main or line noise and muscle tremor noise without much loss in signal strength. This provides a lower order polynomial approximation to the signal, and almost completely removes the 50/60 Hz noise that can interfere with R-peak detection.

Figure 5:
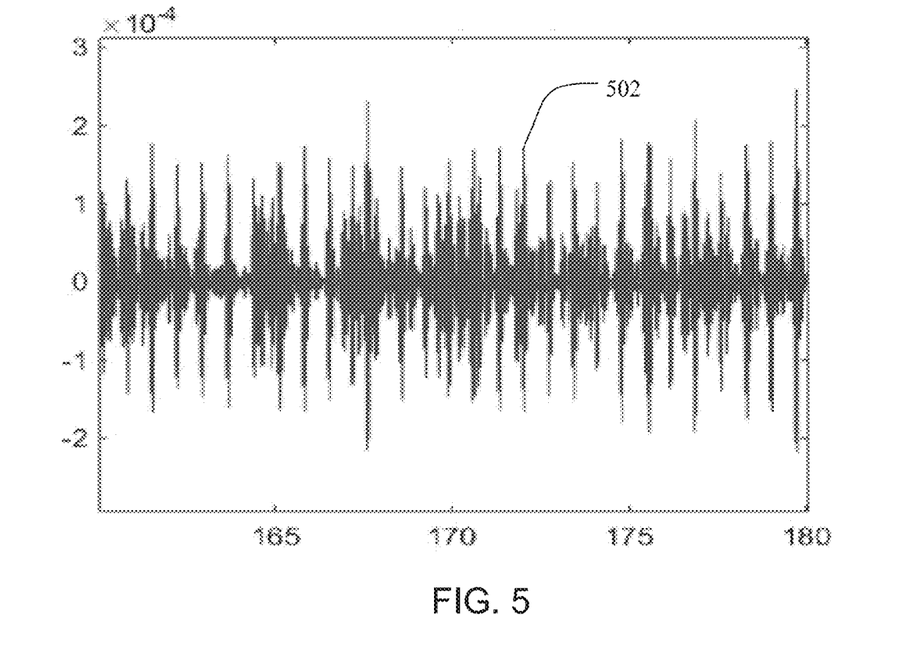
FIG. 5 is a graphical representation of processed ECG data in accordance with an invention embodiment.

In another specific example, R-waves (or peaks) can be extracted by applying a band pass filter to the ECG data. One example of such a filter is a Butterworth filter. Exemplary pass band ranges (i.e. lower cutoff frequency to higher cutoff frequency) can be tailored to a particular situation, and in many cases can be empirically determined by observing the spectral characteristics of noise during the opportunistic recording of the ECG data, which can have a different spectral response than typical motion artifacts in conventional ECG. However, exemplary ranges can include lower and upper cutoff frequencies between 2 Hz and 30 Hz, between 7 Hz and 25 Hz, or between 14 Hz and 22 Hz, among others. In some cases, a pass band frequency range can be chosen that optimizes ECG signal strength and noise level, even if the maximum ECG signal strength is greater at a different frequency range. For example, even though an R-wave frequency band ranges from 2-15 Hz, it may be more effective to use a pass band frequency range of 14-22 Hz because, even though slightly offset, the noise induced by an opportunistic activity such as typing can be multiple times higher than the ECG signal magnitude in the 2-15 Hz range. FIG. 5 shows the filtered ECG data following filtering with a Butterworth filter having a 14-22 Hz passband. ECG R-wave peaks 602 now become more apparent as compared to the raw signal shown in FIG. 4; however, significant noise is still present at this stage, which can interfere with HR measurements.

To further remove the noise, the data can be filtered in the spectral domain. One technique for accomplishing this is by applying a function to the filtered ECG data to transform the data to the time-frequency domain, thus generating time-frequency data. The time-frequency data can then be de-noised. It is noted that the filtered ECG data can be transformed using any function capable of time-frequency domain transformation, all of which are considered to be within the present scope. In one aspect, for example, the function can be a wavelet transformation or wavelet decomposition. Any appropriate wavelet transformation can be used, including stationary wavelet transforms (SWT), discrete wavelet transforms (DWT), and the like. In one specific example the wavelet transform can be a SWT.

One example of a useful SWT can be found in the inbuilt SWT function in the computing environment MATLAB®, by MATHWORKS®. While either SWT or DWT can be used, in some cases SWT may function better, because SWT carries redundant information as it does not down sample the signal at every step. Therefore, SWT is translation invariant, whereas DWT is not translation invariant. This may, in some cases, have implications on the de-noising performance. In DWT, small shifts in the input signal may cause major variations in coefficients at different decomposition levels, and may cause errors in reconstruction.

In some cases it can be helpful to subdivide the filtered ECG data or the time-frequency data into a plurality of subwindows. The wavelet transform can be applied to the data either before or after the subdivision into data subwindows. As one example, filtered ECG can be divided into 1 second windows, or any other convenient duration.

De-noising the time-frequency subwindows can be accomplished by any technique capable of reducing the noise in the data to acceptable levels. As one example, de-noising the time-frequency data can be accomplished by applying a threshold function to the time-frequency data subwindows to generate de-noised time-frequency data subwindows. Applying dynamic thresholding to the subwindows can eliminate frequency components related to noise. In one example, the thresholds for noise elimination in each window can be calculated as per Equation I:

$$\text{Threshold} \propto \text{Median}(\text{abs}(\text{Data}-\text{Median}(\text{Data}))) \quad \text{I}$$

where Data is the time series vector within the is window of the signal.

The section of the signal E that satisfies Equation II $$5*V_{th} > E > 2.5*V_{th} \quad \text{II}$$

in each level are passed to the inverse function for transformation to the time domain. The threshold band calculation is derived using empirical observation, from ECGs acquired opportunistically from several users, that most of the R-peak information is in the band described by Equation II. The wavelet coefficients outside this range are mainly corresponding to the noise, and thus are forced to zero for noise elimination before signal re-construction using the inverse wavelet function. Using this band for thresholding can eliminate most of the noise, but preserves the R-peaks in the re-constructed signal.

The $V_{th}$ threshold is proportional to Median Absolute Deviation (MAD). The constant value is 1.4826, a fraction of MAD. This constant value is useful for eliminating noise from a signal in the wavelet domain. The $V_{th}$ threshold tries to capture the variance of the signal coefficients in the wavelet domain (i.e., the range of the coefficient values corresponding to the signal). This constant usually depends on the distribution of the coefficients. 1.4826 corresponds to a constant value, such that if the distribution of the coefficients was Gaussian then +/−1.4826*MAD will be a range that will capture 70% of the distribution of signal's coefficients.

Figure 6:
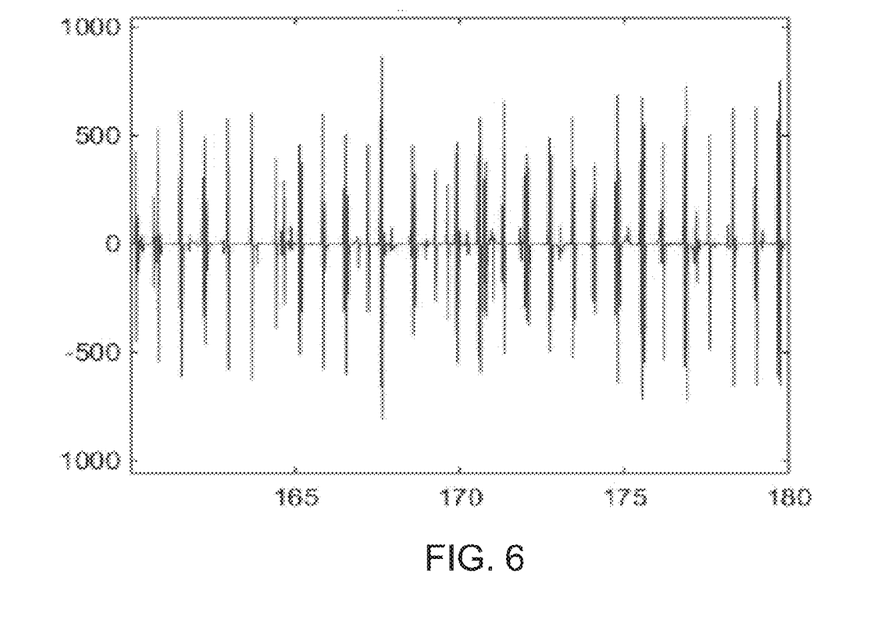
FIG. 6 is a graphical representation of processed ECG data in accordance with an invention embodiment.

In one example, the constant of proportionality can be calculated by observing signal and noise characteristics empirically. The high and low thresholds are maintained to remove both the extremely high amplitude noise impulses during keystrokes and the low intensity noise during usage of touchpad. This thresholding can be done on each wavelet decomposition level separately, and thereafter an inverse wavelet transform (or an inverse function of whatever transform was used) is calculated to re-construct the R-wave peaks. Thus, the de-noised time-frequency data subwindows can be combined to generate the de-noised time-frequency data, and transformed to the time domain using the inverse function to generate the de-noised data. FIG. 6 is an example of de-noised data showing a significant reduction in inter-peak noise compared to FIG. 5.

The wavelet-reconstructed signal shown in FIG. 6 includes both R-wave peaks as well as noise peaks, and even visually it is hard to segregate valid R-peaks from noise peaks. Because noise and R-peaks fall in the same frequency band, separation using spectral characteristics is also not possible. One way to extract an accurate HR from such a signal includes periodicity enhancement using an auto-correlation technique. Thus, in one example deriving the periodicity of a plurality of R peaks can be accomplished by auto-correlating the de-noised data to generate auto-correlated peak data. However, while an auto-correlation technique alone can enhance periodicity in a signal when the signal and the noise are of fairly comparable magnitude, opportunistically sensed ECG signals often include noise that is several times the magnitude of the ECG signal. This signal to noise ratio can render auto-correlation techniques alone ineffective.

Figure 7:
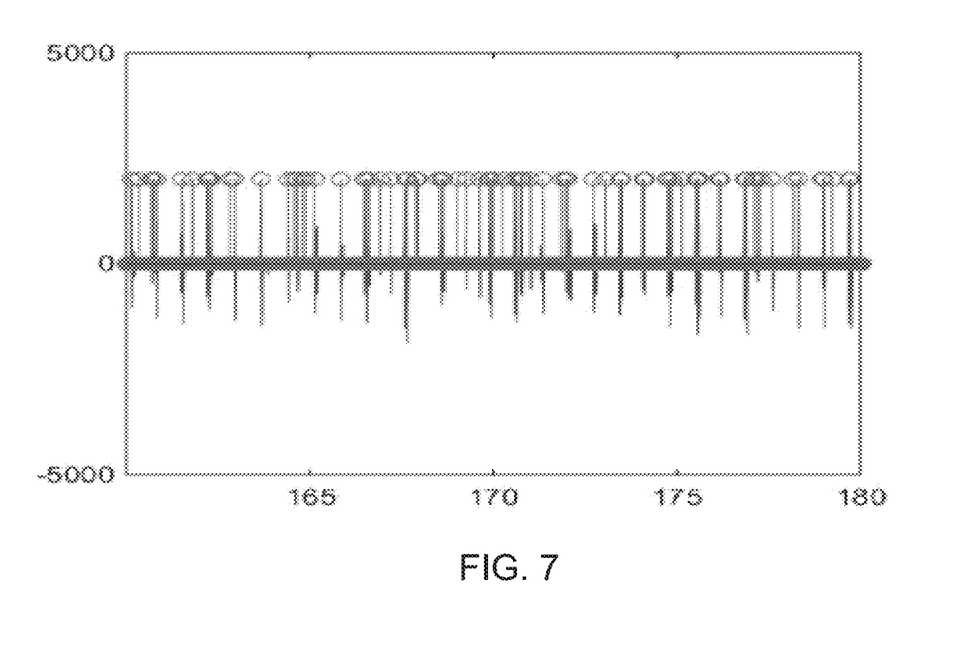
FIG. 7 is a graphical representation of processed ECG data in accordance with an invention embodiment.

Various techniques can be utilized along with auto-correlation to effectively enhance the periodicity of the de-noised data. In one example technique, the plurality of peaks are identified in the data (the R-peaks and the noise peaks) to generate peak data. The identification of peaks can be accomplished by any suitable method. For example, applying a window function or a threshold function to the data can generate useful peak data. Next, a binary function is applied to the peak data to generate binary data comprising binary peaks and binary non-peaks, or in other words, data in which the peaks are represented by ones, and all other data points (or no-peaks) are represented by zeros. Depending on the technique utilized to identify the peaks, applying a binary function may not be needed, as the output of the peak-identification technique may already be a binary representation. Regardless, the representation assigns uniform weight (i.e. value 1) to both valid R-wave peaks as well as noise peaks, irrespective of their magnitudes. This creates a representation suitable for increasing the effectiveness of correlation-based periodicity extraction. FIG. 7 shows an example of such a binary representation of detected peaks, in which it is still difficult to even visually discern the periodicity of the HR.

Figure 8:
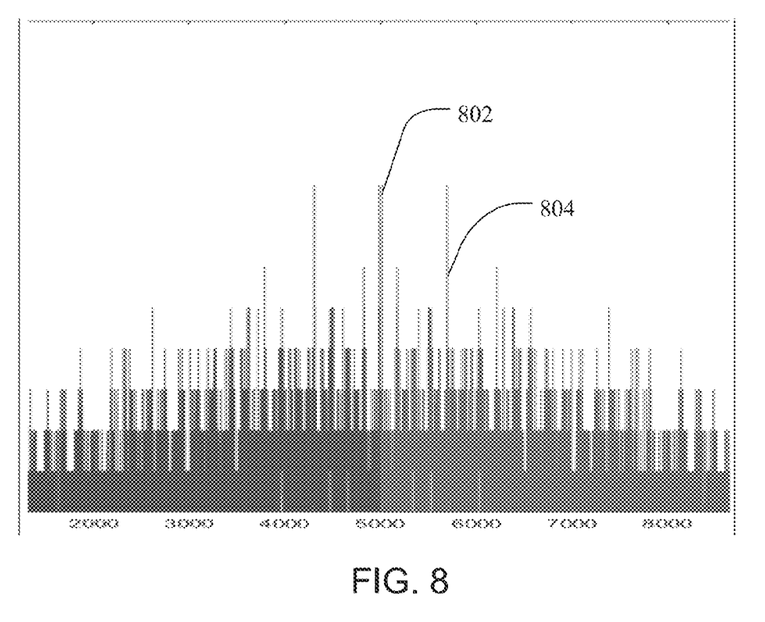
FIG. 8 is a graphical representation of processed ECG data in accordance with an invention embodiment.

Once converted to this normalized binary scale, the binary data is auto-correlated to generate or enhance the periodicity of the R-peaks, while automatically filtering out the non-periodic noise peaks. FIG. 8 shows an example of the auto-correlated binary peak data, where the $1^{st}$ dominant peak 802 and an apparent $2^{nd}$ dominant peak 804 can be seen. Typically, the waveform of an auto-correlation function has a $2^{nd}$ dominant peak at the most periodic component in the signal, which is equal to the R-wave periodicity. However, due to the binary nature of the input signal, the energy of the $2^{nd}$ dominant peak is spread out in extremely noisy situations, thereby making the true $2^{nd}$ dominant peak detection obscure. This effect is shown in FIG. 8, where the true period of the R-wave is not reflected by the apparent $2^{nd}$ dominant peak 804.

Figure 9:
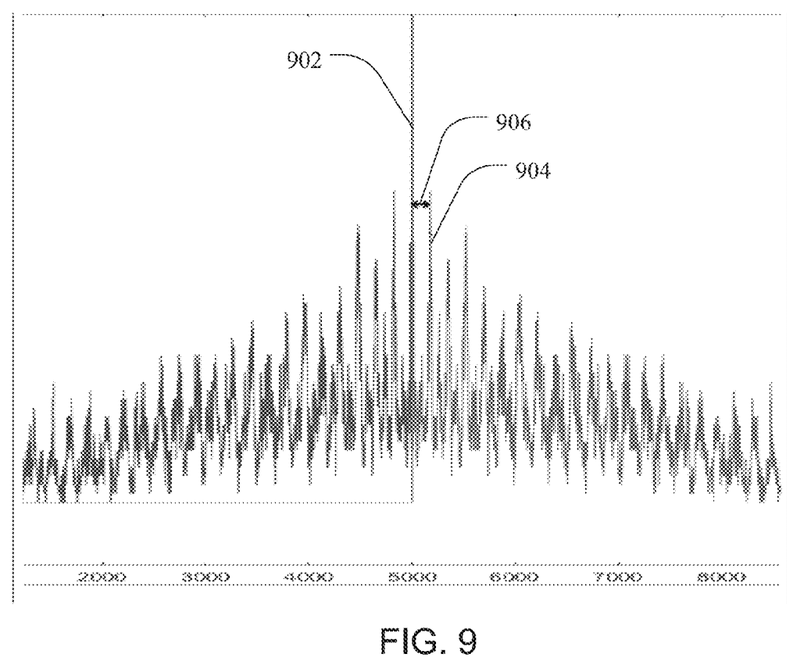
FIG. 9 is a graphical representation of processed ECG data in accordance with an invention embodiment.

To aggregate the mean energy spread in the binary auto-correlation signal from FIG. 8, the auto-correlated peak data can be smoothed to enhance the $2^{nd}$ dominant peak of the auto-correlated peak data. Thus, by correcting for the energy spread that was introduced by the binary input, the true $2^{nd}$ dominant peak is realized. FIG. 9 shows an example of auto-correlated peak data that has been smoothed by applying a Savitzky-Golay filter to the data where the $1^{st}$ dominant peak 902 and the true $2^{nd}$ dominant peak 904 can be clearly seen. This processed autocorrelation data aggregates the energy spread and enhances the true periodicity as a $2^{nd}$ dominant peak 904. The distance 906 (time interval) between the $1^{st}$ dominant peak 902 (the central peak) and the $2^{nd}$ dominant peak 904 of the smoothened auto-correlation signal is the same as R-to-R wave interval from which true HR can be computed. It is noted that any technique for smoothing or otherwise aggregating the energy spread is considered to be within the present scope. For example, various low pass filters can be utilized to smooth the auto-correlated data.

In another example, the issue of energy spread of the $2^{nd}$ dominant peak can be avoided through a slightly different data processing procedure. In this case, the plurality of peaks are identified in the data (the R-peaks and the noise peaks) to generate peak data as described above. Once the peaks have been identified, a Gaussian curve is applied to each peak of the peak data to generate Gaussian peak data. The Gaussian peak data can then be auto-correlated to generate auto-correlated peak data. The auto-correlation of the Gaussian peak data does not have the problem of energy spread, and therefore the true $2^{nd}$ dominant peak is readily apparent in the output of the auto-correlation.

Once the $1^{st}$ dominant peak and the $2^{nd}$ dominant peak are realized, the distance between the two can be measured to provide the HR of the subject.

Approaches in accordance with invention embodiments can be implemented on a variety of devices, systems, and by various methods. In one example, a device for determining HR of a subject from noisy ECG data is provided. Such a device can comprise circuitry configured to, referencing FIG. 2, 202 filter incoming ECG data to generate filtered ECG data, 204 transform, using a function, the filtered ECG data to a time-frequency domain to generate time-frequency data, 206 de-noise the time-frequency data to generate de-noised time-frequency data, 208 transform, using an inverse function, the de-noised time-frequency data to a time domain to generate de-noised data, 210 identify a plurality of peaks in the de-noised data, 212 derive a periodicity of a plurality of R peaks from the plurality of peaks, and 214 derive the HR of the subject from the periodicity of the plurality of R peaks. In another example, the circuitry can further comprise an input channel to receive the incoming ECG data. The input channel can be a wired channel, or a wireless channel. Wireless channels can include wireless network channels, Bluetooth channels, cellular channels, optical channels, and the like. In yet another example, the circuitry can be further configured to generate a notification of the derived HR and send the notification to an output channel.

In another example, a non-transitory machine readable storage medium is provided having instructions embodied thereon for determining HR of a subject from noisy ECG data, the instructions when executed perform, referencing FIG. 2, 202 filtering incoming ECG data to generate filtered ECG data, 204 transforming, using a function, the filtered ECG data to a time-frequency domain to generate time-frequency data, 206 de-noising the time-frequency data to generate de-noised time-frequency data, 208 transforming, using an inverse function, the de-noised time-frequency data to a time domain to generate de-noised data, 210 identifying a plurality of peaks in the de-noised data, 212 deriving a periodicity of a plurality of R peaks from the plurality of peaks, and 214 deriving the HR of the subject from the periodicity of the plurality of R peaks. In another example, the non-transitory machine readable storage medium further includes instructions that when executed generate a notification of the derived HR and send the notification to an output channel.

Figure 10:
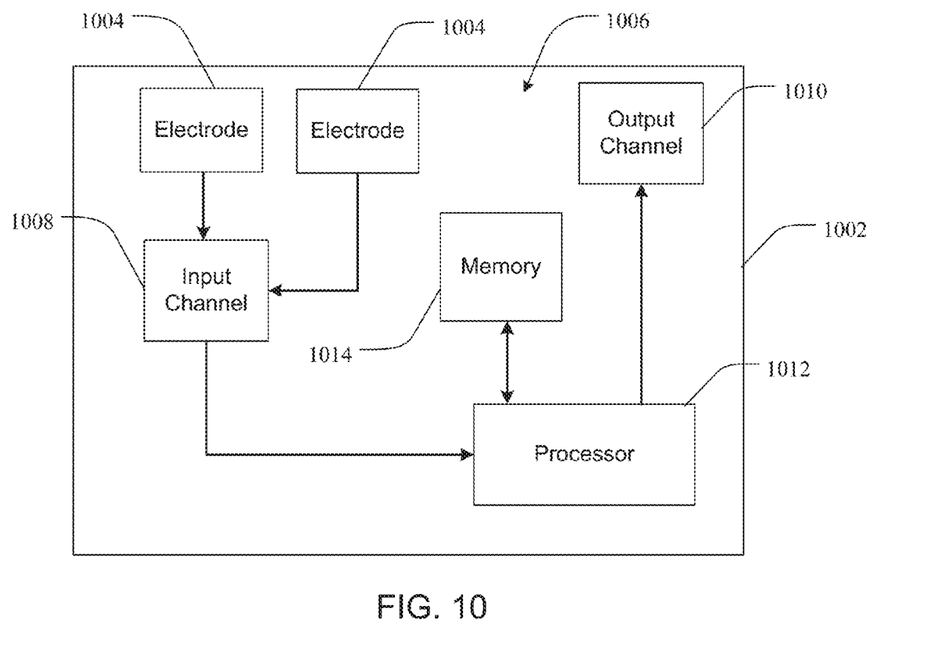
FIG. 10 is a block diagram view of system for determining HR of a subject from noisy ECG data in accordance with an invention embodiment.

In yet another example, a system for determining HR of a subject from noisy ECG data is provided, one implementation of which is shown in FIG. 10. The system comprises a usable object 1002 configured for physically interactive use by a subject, and at least two electrodes 1004 coupled to the usable object 1002 and positioned to facilitate ECG data recording from the subject. In one specific example, the at least two electrodes 1004 are positioned relative to the usable object 1002 such that the ECG data recording is opportunistic ECG data recording. In other examples, the ECG data recording is intentional ECG data recording.

The system can additionally include circuitry 1006, shown generally throughout FIG. 10, and including an input channel 1008 coupled to the at least two electrodes 1004. The circuitry 1006 is configured to, referencing FIG. 2, 202 filter incoming ECG data to generate filtered ECG data, 204 transform, using a function, the filtered ECG data to a time-frequency domain to generate time-frequency data, 206 de-noise the time-frequency data to generate de-noised time-frequency data, 208 transform, using an inverse function, the de-noised time-frequency data to a time domain to generate de-noised data, 210 identify a plurality of peaks in the de-noised data, 212 derive a periodicity of a plurality of R peaks from the plurality of peaks, and 214 derive the HR of the subject from the periodicity of the plurality of R peaks. In another example, the circuitry 1006 of the system is further configured to generate a notification of the derived HR and send the notification to an output channel 1010. The circuitry can also be configured to include one or more processors 1012 and at least one memory 1014 or a non-transitory machine readable storage medium. Additionally, the system can be configured such that the electrodes and the circuitry are resident on the useable object. The system can also be configured such that the circuitry or a portion thereof is located at a remote location from the electrodes and the usable object. As such, the electrodes acquire ECG data from the subject, which is transmitted to the remote location for processing.

The usable object 1002 can include any object, device, system, or apparatus that is held or otherwise used by a subject in a manner that allows an ECG signal to be recorded from the subject. Non-limiting examples can include computer keyboards, computer mice, joysticks, gamepads, laptops, tablet PCs, smart phones and other mobile devices, exercise equipment, vehicle steering wheels, wheel chairs, bed side rails, handrails, wearable sensors, and the like, including appropriate combinations thereof.

The various system examples described herein can generally include a processor in communication with a memory, an input channel, and an output channel. As used herein, the term processor can include one or more general purpose processors, specialized processors such as VLSI, FPGAs, or other types of specialized processors, such as Integrated Sensor Hub (ISH) processors. ISH processors allow efficient and continuous data acquisition and analysis, with minimal power consumption.

Memory can include any device, combination of devices, circuitry, and the like that is capable of storing, accessing, organizing and/or retrieving data. Non-limiting examples include SANs (Storage Area Network), cloud storage networks, volatile or non-volatile RAM, phase change memory, optical media, hard-drive type media, and the like, including combinations thereof.

Systems can also include a local communication interface for connectivity between the various components of a given system. For example, the local communication interface can be a local data bus and/or any related address or control busses as may be desired.

Systems can also include an I/O (input/output) interface for controlling the I/O functions of the system, as well as for I/O connectivity to devices outside of the system. In some examples, one or both of the input channel and the output channel can be a part of the I/O interface. A network interface can also be included for network connectivity. The network interface can control network communications both within the system and outside of the system. The network interface can include a wired interface, a wireless interface, a Bluetooth interface, optical interface, cellular interface, and the like, including appropriate combinations thereof. Furthermore, a system can additionally include a user interface, a display device, as well as various other components that would be beneficial for such a system.

Various techniques, or certain aspects or portions thereof, can take the form of program code (i.e., instructions) embodied in tangible media, such as floppy diskettes, compact disc-read-only memory (CD-ROMs), hard drives, non-transitory computer readable storage medium, or any other machine-readable storage medium wherein, when the program code is loaded into and executed by a machine, such as a computer, the machine becomes an apparatus for practicing the various techniques. Circuitry can include hardware, firmware, program code, executable code, computer instructions, and/or software. A non-transitory computer readable storage medium can be a computer readable storage medium that does not include signal. In the case of program code execution on programmable computers, the computing device can include a processor, a storage medium readable by the processor (including volatile and non-volatile memory and/or storage elements), at least one input device, and at least one output device. The volatile and non-volatile memory and/or storage elements can be a random-access memory (RAM), erasable programmable read only memory (EPROM), flash drive, optical drive, magnetic hard drive, solid state drive, or other medium for storing electronic data. One or more programs that can implement or utilize the various techniques described herein can use an application programming interface (API), reusable controls, and the like. Such programs can be implemented in a high level procedural or object oriented programming language to communicate with a computer system. However, the program(s) can be implemented in assembly or machine language, if desired. In any case, the language can be a compiled or interpreted language, and combined with hardware implementations.

EXAMPLES

The following examples pertain to specific invention embodiments and point out specific features, elements, or steps that can be used or otherwise combined in achieving such embodiments.

In an example there is provided a device for determining heart rate (HR) of a subject from noisy Electrocardiogram (ECG) data, the device comprising circuitry configured to:
filter incoming ECG data to generate filtered ECG data;
transform, using a function, the filtered ECG data to a time-frequency domain to generate time-frequency data;

de-noise the time-frequency data to generate de-noised time-frequency data;

transform, using an inverse function, the de-noised time-frequency data to a time domain to generate de-noised data;

identify a plurality of peaks in the de-noised data;

derive a periodicity of a plurality of R peaks from the plurality of peaks; and derive the HR of the subject from the periodicity of the plurality of R peaks.

In an example of a device for determining HR of a subject from noisy ECG data, filtering the ECG data further comprises filtering the ECG data with a low pass filter.

In an example of a device for determining HR of a subject from noisy ECG data, the low pass filter has a cutoff frequency of 30 Hz or less.

In an example of a device for determining HR of a subject from noisy ECG data, the low pass filter has a cutoff frequency of 25 Hz or less.

In an example of a device for determining HR of a subject from noisy ECG data, the low pass filter has a cutoff frequency of 22 Hz or less.

In an example of a device for determining HR of a subject from noisy ECG data, the low pass filter is of order 2 or more.

In an example of a device for determining HR of a subject from noisy ECG data, the low pass filter is of order 5 or more.

In an example of a device for determining HR of a subject from noisy ECG data, the low pass filter is of order 8 or more.

In an example of a device for determining HR of a subject from noisy ECG data, filtering the ECG data further comprises filtering the ECG data with a band pass filter.

In an example of a device for determining HR of a subject from noisy ECG data, the band pass filter has a lower cutoff frequency of 2 Hz or more and an upper cutoff frequency of 30 Hz or less.

In an example of a device for determining HR of a subject from noisy ECG data, the band pass filter has a lower cutoff frequency of 7 Hz or more and an upper cutoff frequency of 25 Hz or less.

In an example of a device for determining HR of a subject from noisy ECG data, the band pass filter has a lower cutoff frequency of 14 Hz or more and an upper cutoff frequency of 22 Hz or less.

In an example of a device for determining HR of a subject from noisy ECG data, the band pass filter is of order 2 or more.

In an example of a device for determining HR of a subject from noisy ECG data, the band pass filter is of order 5 or more.

In an example of a device for determining HR of a subject from noisy ECG data, the band pass filter is of order 8 or more.

In an example of a device for determining HR of a subject from noisy ECG data, filtering the ECG data further comprises filtering the ECG data with a low pass filter and a band pass filter.

In an example of a device for determining HR of a subject from noisy ECG data, the circuitry is further configured to filter the incoming ECG data using an infinite impulse response (IIR) filter.

In an example of a device for determining HR of a subject from noisy ECG data, the circuitry is further configured to filter the incoming ECG data using a finite impulse response (FIR) filter.

In an example of a device for determining HR of a subject from noisy ECG data, the circuitry is further configured to filter the incoming ECG data using a filter selected from the group consisting of Savitzky-Golay filters, Elliptic filter, Chebyshev filters, Butterworth filters, Bessel filters, and combinations thereof.

In an example of a device for determining HR of a subject from noisy ECG data, the circuitry is further configured to filter the incoming ECG data using a Savitzky-Golay filter.

In an example of a device for determining HR of a subject from noisy ECG data, the circuitry is further configured to filter the incoming ECG data using a Butterworth filter.

In an example of a device for determining HR of a subject from noisy ECG data, the circuitry is further configured to include an input channel to receive the incoming ECG data.

In an example of a device for determining HR of a subject from noisy ECG data, the function includes a wavelet transform.

In an example of a device for determining HR of a subject from noisy ECG data, the wavelet transform is a stationary wavelet transform.

In an example of a device for determining HR of a subject from noisy ECG data, the wavelet transform is a discrete wavelet transform.

In an example of a device for determining HR of a subject from noisy ECG data, in applying the transform to the filtered ECG data, the circuitry is further configured to:

divide the filtered ECG data into a plurality of filtered ECG data subwindows; and apply the wavelet transform to at least a portion of the plurality of ECG data subwindows to generate a plurality of time-frequency data subwindows.

In an example of a device for determining HR of a subject from noisy ECG data, in de-noising the time-frequency data, the circuitry is further configured to apply a threshold function to the time-frequency data subwindows to generate de-noised time-frequency data subwindows.

In an example of a device for determining HR of a subject from noisy ECG data, the inverse function is an inverse wavelet function.

In an example of a device for determining HR of a subject from noisy ECG data, in transforming the de-noised time-frequency data, the circuitry is further configured to:

combine the de-noised time-frequency data subwindows to generate the de-noised time-frequency data; and transform, using the inverse function, the de-noised time-frequency data to the time domain to generate the de-noised data.

In an example of a device for determining HR of a subject from noisy ECG data, in identify the plurality of peaks and deriving the periodicity of the plurality of R peaks, the circuitry is further configured to auto-correlate the de-noised data to generate auto-correlated peak data.

In an example of a device for determining HR of a subject from noisy ECG data, in deriving HR of the subject, the circuitry is further configured to calculate a distance from a first dominant peak to a second dominant peak of the auto-correlated peak data.

In an example of a device for determining HR of a subject from noisy ECG data, in identifying the plurality of peaks, the circuitry is further configured to apply a window function to the data to generate peak data.

In an example of a device for determining HR of a subject from noisy ECG data, in deriving the periodicity of the plurality of R peaks, the circuitry is further configured to:

apply a binary function to the peak data to generate binary data comprising binary peaks and binary non-peaks; and auto-correlate the binary data to derive the periodicity of the R-peaks.

In an example of a device for determining HR of a subject from noisy ECG data, the circuitry is further configured to smooth the auto-correlated peak data to enhance a second dominant peak of the auto-correlated peak data.

In an example of a device for determining HR of a subject from noisy ECG data, in smoothing the auto-correlated peak data, the circuitry is further configured to smooth the auto-correlated binary peak data by applying a low pass filter to the auto-correlated peak data.

In an example of a device for determining HR of a subject from noisy ECG data, in smoothing the auto-correlated peak data, the circuitry is further configured to apply a Savitzky-Golay filter to the auto-correlated peak data.

In an example of a device for determining HR of a subject from noisy ECG data, in deriving the HR of the subject, the circuitry is further configured to calculate a distance from a first dominant peak to the second dominant peak of the auto-correlated peak data.

In an example of a device for determining HR of a subject from noisy ECG data, in deriving the periodicity of the plurality of R peaks, the circuitry is further configured to:
  apply a Gaussian curve to each peak of the peak data to generate Gaussian peak data; and
  auto-correlate the Gaussian peak data to generate auto-correlated peak data from which to derive the periodicity of the R-peaks.

In an example of a device for determining HR of a subject from noisy ECG data, in deriving the HR of the subject, the circuitry is further configured to calculate a distance from a first dominant peak to a second dominant peak of the auto-correlated peak data.

In an example of a device for determining HR of a subject from noisy ECG data, the circuitry is further configured to:
  generate a notification of the derived HR; and
  send the notification to an output channel.

In one example there is provided a non-transitory machine readable storage medium having instructions embodied thereon for determining heart rate (HR) of a subject from noisy Electrocardiogram (ECG) data, the instructions when executed perform the following:
  filtering incoming ECG data to generate filtered ECG data;
  transforming, using a function, the filtered ECG data to a time-frequency domain to generate time-frequency data;
  de-noising the time-frequency data to generate de-noised time-frequency data;
  transforming, using an inverse function, the de-noised time-frequency data to a time domain to generate de-noised data;
  identifying a plurality of peaks in the de-noised data;
  deriving a periodicity of a plurality of R peaks from the plurality of peaks; and
  deriving the HR of the subject from the periodicity of the plurality of R peaks.

In one example, filtering the ECG data of the non-transitory machine readable storage medium further comprises filtering the ECG data with a low pass filter.

In one example, the low pass filter of the non-transitory machine readable storage medium has a cutoff frequency of 30 Hz or less.

In one example, the low pass filter of the non-transitory machine readable storage medium has a cutoff frequency of 25 Hz or less.

In one example, the low pass filter of the non-transitory machine readable storage medium has a cutoff frequency of 22 Hz or less.

In one example, the low pass filter of the non-transitory machine readable storage medium is of order 2 or more.

In one example, the low pass filter of the non-transitory machine readable storage medium is of order 5 or more.

In one example, the low pass filter of the non-transitory machine readable storage medium is of order 8 or more.

In one example of the non-transitory machine readable storage medium, filtering the ECG data further comprises filtering the ECG data with a band pass filter.

In one example of the non-transitory machine readable storage medium, the band pass filter has a lower cutoff frequency of 2 Hz or more and an upper cutoff frequency of 30 Hz or less.

In one example of the non-transitory machine readable storage medium, the band pass filter has a lower cutoff frequency of 7 Hz or more and an upper cutoff frequency of 25 Hz or less.

In one example of the non-transitory machine readable storage medium, the band pass filter has a lower cutoff frequency of 14 Hz or more and an upper cutoff frequency of 22 Hz or less.

In one example of the non-transitory machine readable storage medium, the band pass filter is of order 2 or more.

In one example of the non-transitory machine readable storage medium, the band pass filter is of order 5 or more.

In one example of the non-transitory machine readable storage medium, the band pass filter is of order 8 or more.

In one example of the non-transitory machine readable storage medium, filtering the ECG data further comprises filtering the ECG data with a low pass filter and a band pass filter.

In one example the non-transitory machine readable storage medium, further comprises instructions that when executed filter the incoming ECG data using an infinite impulse response (IIR) filter.

In one example of the non-transitory machine readable storage medium, the circuitry is further configured to filter the incoming ECG data using a finite impulse response (FIR) filter.

In one example the non-transitory machine readable storage medium, further comprises instructions that when executed filter the incoming ECG data using a filter selected from the group consisting of Savitzky-Golay filters, Elliptic filter, Chebyshev filters, Butterworth filters, Bessel filters, and combinations thereof.

In one example the non-transitory machine readable storage medium, further comprises instructions that when executed filter the incoming ECG data using a Savitzky-Golay filter.

In one example the non-transitory machine readable storage medium, further comprises instructions that when executed filter the incoming ECG data using a Butterworth filter.

In one example of the non-transitory machine readable storage medium, the function includes a wavelet transform.

In one example of the non-transitory machine readable storage medium, the wavelet transform is a stationary wavelet transform.

In one example of the non-transitory machine readable storage medium, the wavelet transform is a discrete wavelet transform.

In one example of the non-transitory machine readable storage medium, applying the transform to the filtered ECG data, the non-transitory machine readable storage medium further comprises instructions that when executed:
    divide the filtered ECG data into a plurality of filtered ECG data subwindows; and
    apply the wavelet transform to at least a portion of the plurality of ECG data subwindows to generate a plurality of time-frequency data subwindows.

In one example of the non-transitory machine readable storage medium, de-noising the time-frequency data, the non-transitory machine readable storage medium further comprises instructions that when executed apply a threshold function to the time-frequency data subwindows to generate de-noised time-frequency data subwindows.

In one example of the non-transitory machine readable storage medium, the inverse function is an inverse wavelet function.

In one example of the non-transitory machine readable storage medium, in transforming the de-noised time-frequency data, the non-transitory machine readable storage medium further comprises instructions that when executed:
    combine the de-noised time-frequency data subwindows to generate the de-noised time-frequency data; and
    transform, using the inverse function, the de-noised time-frequency data to the time domain to generate the de-noised data.

In one example of the non-transitory machine readable storage medium, identifying the plurality of peaks and deriving the periodicity of the plurality of R peaks, the non-transitory machine readable storage medium further comprises instructions that when executed auto-correlate the de-noised data to generate auto-correlated peak data.

In one example of the non-transitory machine readable storage medium, deriving HR of the subject, the non-transitory machine readable storage medium further comprises instructions that when executed calculate a distance from a first dominant peak to a second dominant peak of the auto-correlated peak data.

In one example of the non-transitory machine readable storage medium, identifying the plurality of peaks, the non-transitory machine readable storage medium further comprises instructions that when executed apply a window function to the data to generate peak data.

In one example of the non-transitory machine readable storage medium, deriving the periodicity of the plurality of R peaks, the non-transitory machine readable storage medium further comprises instructions that when executed:
    apply a binary function to the peak data to generate binary data comprising binary peaks and binary non-peaks; and
    auto-correlate the binary data to derive the periodicity of the R-peaks.

In one example the non-transitory machine readable storage medium further comprises instructions that when executed smooth the auto-correlated peak data to enhance a second dominant peak of the auto-correlated peak data.

In one example of the non-transitory machine readable storage medium, smoothing the auto-correlated peak data, the non-transitory machine readable storage medium further comprises instructions that when executed smooth the auto-correlated binary peak data by applying a low pass filter to the auto-correlated peak data.

In one example of the non-transitory machine readable storage medium, smoothing the auto-correlated peak data, the non-transitory machine readable storage medium further comprises instructions that when executed apply a Savitzky-Golay filter to the auto-correlated peak data.

In one example of the non-transitory machine readable storage medium, deriving the HR of the subject, the non-transitory machine readable storage medium further comprises instructions that when executed calculate a distance from a first dominant peak to the second dominant peak of the auto-correlated peak data.

In one example of the non-transitory machine readable storage medium, deriving the periodicity of the plurality of R peaks, the non-transitory machine readable storage medium further comprises instructions that when executed:
    apply a Gaussian curve to each peak of the peak data to generate Gaussian peak data; and
    auto-correlate the Gaussian peak data to generate auto-correlated peak data from which to derive the periodicity of the R-peaks.

In one example of the non-transitory machine readable storage medium, deriving the HR of the subject, the non-transitory machine readable storage medium further comprises instructions that when executed calculate a distance from a first dominant peak to a second dominant peak of the auto-correlated peak data.

In one example, the non-transitory machine readable storage medium, further comprises instructions that when executed:
    generate a notification of the derived HR; and
    send the notification to an output channel.

In one example there is provided a system for determining heart rate (HR) of a subject from noisy Electrocardiogram (ECG) data, comprising:
    a usable object configured for physically interactive use by a subject;
    at least two electrodes coupled to the usable object and positioned to facilitate ECG data recording from the subject;
    circuitry including an input channel coupled to the at least two electrodes, the circuitry being configured to:
        filter incoming ECG data to generate filtered ECG data;
        transform, using a function, the filtered ECG data to a time-frequency domain to generate time-frequency data;
        de-noise the time-frequency data to generate de-noised time-frequency data;
        transform, using an inverse function, the de-noised time-frequency data to a time domain to generate de-noised data;
        identify a plurality of peaks in the de-noised data;
        derive a periodicity of a plurality of R peaks from the plurality of peaks; and
        derive the HR of the subject from the periodicity of the plurality of R peaks.

In one example of a system for determining heart rate (HR) of a subject from noisy Electrocardiogram, filtering the ECG data further comprises filtering the ECG data with a low pass filter.

In one example of a system for determining heart rate (HR) of a subject from noisy Electrocardiogram, the low pass filter has a cutoff frequency of 30 Hz or less.

In one example of a system for determining heart rate (HR) of a subject from noisy Electrocardiogram, the low pass filter has a cutoff frequency of 25 Hz or less.

In one example of a system for determining heart rate (HR) of a subject from noisy Electrocardiogram, the low pass filter has a cutoff frequency of 22 Hz or less.

In one example of a system for determining heart rate (HR) of a subject from noisy Electrocardiogram, the low pass filter is of order 2 or more.

In one example of a system for determining heart rate (HR) of a subject from noisy Electrocardiogram, the low pass filter is of order 5 or more.

In one example of a system for determining heart rate (HR) of a subject from noisy Electrocardiogram, the low pass filter is of order 8 or more.

In one example of a system for determining heart rate (HR) of a subject from noisy Electrocardiogram, filtering the ECG data further comprises filtering the ECG data with a band pass filter.

In one example of a system for determining heart rate (HR) of a subject from noisy Electrocardiogram, the band pass filter has a lower cutoff frequency of 2 Hz or more and an upper cutoff frequency of 30 Hz or less.

In one example of a system for determining heart rate (HR) of a subject from noisy Electrocardiogram, the band pass filter has a lower cutoff frequency of 7 Hz or more and an upper cutoff frequency of 25 Hz or less.

In one example of a system for determining heart rate (HR) of a subject from noisy Electrocardiogram, the band pass filter has a lower cutoff frequency of 14 Hz or more and an upper cutoff frequency of 22 Hz or less.

In one example of a system for determining heart rate (HR) of a subject from noisy Electrocardiogram, the band pass filter is of order 2 or more.

In one example of a system for determining heart rate (HR) of a subject from noisy Electrocardiogram, the band pass filter is of order 5 or more.

In one example of a system for determining heart rate (HR) of a subject from noisy Electrocardiogram, the band pass filter is of order 8 or more.

In one example of a system for determining heart rate (HR) of a subject from noisy Electrocardiogram, filtering the ECG data further comprises filtering the ECG data with a low pass filter and a band pass filter.

In one example of a system for determining heart rate (HR) of a subject from noisy Electrocardiogram, the circuitry is further configured to filter the incoming ECG data using an infinite impulse response (IIR) filter.

In one example of a system for determining heart rate (HR) of a subject from noisy Electrocardiogram, the circuitry is further configured to filter the incoming ECG data using a finite impulse response (FIR) filter.

In one example of a system for determining heart rate (HR) of a subject from noisy Electrocardiogram, the circuitry is further configured to filter the incoming ECG data using a filter selected from the group consisting of Savitzky-Golay filters, Elliptic filter, Chebyshev filters, Butterworth filters, Bessel filters, and combinations thereof.

In one example of a system for determining heart rate (HR) of a subject from noisy Electrocardiogram, the circuitry is further configured to filter the incoming ECG data using a Savitzky-Go lay filter.

In one example of a system for determining heart rate (HR) of a subject from noisy Electrocardiogram, the circuitry is further configured to filter the incoming ECG data using a Butterworth filter.

In one example of a system for determining heart rate (HR) of a subject from noisy Electrocardiogram, the circuitry is further configured to include an input channel to receive the incoming ECG data.

In one example of a system for determining heart rate (HR) of a subject from noisy Electrocardiogram, the function includes a wavelet transform.

In one example of a system for determining heart rate (HR) of a subject from noisy Electrocardiogram, the wavelet transform is a stationary wavelet transform.

In one example of a system for determining heart rate (HR) of a subject from noisy Electrocardiogram, the wavelet transform is a discrete wavelet transform.

In one example of a system for determining heart rate (HR) of a subject from noisy Electrocardiogram, applying the transform to the filtered ECG data, the circuitry is further configured to:
divide the filtered ECG data into a plurality of filtered ECG data subwindows; and
apply the wavelet transform to at least a portion of the plurality of ECG data subwindows to generate a plurality of time-frequency data subwindows.

In one example of a system for determining heart rate (HR) of a subject from noisy Electrocardiogram, de-noising the time-frequency data, the circuitry is further configured to apply a threshold function to the time-frequency data subwindows to generate de-noised time-frequency data subwindows.

In one example of a system for determining heart rate (HR) of a subject from noisy Electrocardiogram, the inverse function is an inverse wavelet function.

In one example of a system for determining heart rate (HR) of a subject from noisy Electrocardiogram, transforming the de-noised time-frequency data, the circuitry is further configured to:
combine the de-noised time-frequency data subwindows to generate the de-noised time-frequency data; and
transform, using the inverse function, the de-noised time-frequency data to the time domain to generate the de-noised data.

In one example of a system for determining heart rate (HR) of a subject from noisy Electrocardiogram, identify the plurality of peaks and deriving the periodicity of the plurality of R peaks, the circuitry is further configured to auto-correlate the de-noised data to generate auto-correlated peak data.

In one example of a system for determining heart rate (HR) of a subject from noisy Electrocardiogram, deriving HR of the subject, the circuitry is further configured to calculate a distance from a first dominant peak to a second dominant peak of the auto-correlated peak data.

In one example of a system for determining heart rate (HR) of a subject from noisy Electrocardiogram, identifying the plurality of peaks, the circuitry is further configured to apply a window function to the data to generate peak data.

In one example of a system for determining heart rate (HR) of a subject from noisy Electrocardiogram, deriving the periodicity of the plurality of R peaks, the circuitry is further configured to:
apply a binary function to the peak data to generate binary data comprising binary peaks and binary non-peaks; and
auto-correlate the binary data to derive the periodicity of the R-peaks.

In one example of a system for determining heart rate (HR) of a subject from noisy Electrocardiogram, the circuitry is further configured to smooth the auto-correlated peak data to enhance a second dominant peak of the auto-correlated peak data.

In one example of a system for determining heart rate (HR) of a subject from noisy Electrocardiogram, smoothing the auto-correlated peak data, the circuitry is further configured to smooth the auto-correlated binary peak data by applying a low pass filter to the auto-correlated peak data.

In one example of a system for determining heart rate (HR) of a subject from noisy Electrocardiogram, smoothing the auto-correlated peak data, the circuitry is further configured to apply a Savitzky-Go lay filter to the auto-correlated peak data.

In one example of a system for determining heart rate (HR) of a subject from noisy Electrocardiogram, deriving the HR of the subject, the circuitry is further configured to calculate a distance from a first dominant peak to the second dominant peak of the auto-correlated peak data.

In one example of a system for determining heart rate (HR) of a subject from noisy Electrocardiogram, deriving the periodicity of the plurality of R peaks, the circuitry is further configured to:
apply a Gaussian curve to each peak of the peak data to generate Gaussian peak data; and
auto-correlate the Gaussian peak data to generate auto-correlated peak data from which to derive the periodicity of the R-peaks.

In one example of a system for determining heart rate (HR) of a subject from noisy Electrocardiogram, deriving the HR of the subject, the circuitry is further configured to calculate a distance from a first dominant peak to a second dominant peak of the auto-correlated peak data.

In one example of a system for determining heart rate (HR) of a subject from noisy Electrocardiogram, the circuitry is further configured to:
generate a notification of the derived HR; and
send the notification to an output channel.

In one example of a system for determining heart rate (HR) of a subject from noisy Electrocardiogram, the at least two electrodes are positioned relative to the object such that the ECG data recording is opportunistic ECG data recording.

In one example of a system for determining heart rate (HR) of a subject from noisy Electrocardiogram, the usable object includes an object selected from the group consisting of computer keyboards, computer mice, laptops, tablet PCs, smart phones, exercise equipment, automobile steering wheels, wheel chairs, bed side rails, and combinations thereof.

In one example there is provided, a method for determining heart rate (HR) of a subject from noisy Electrocardiogram (ECG) data, comprising:
filtering incoming ECG data to generate filtered ECG data;
transforming, using a function, the filtered ECG data to a time-frequency domain to generate time-frequency data;
de-noising the time-frequency data to generate de-noised time-frequency data;
transforming, using an inverse function, the de-noised time-frequency data to a time domain to generate de-noised data;
identifying a plurality of peaks in the de-noised data;
deriving a periodicity of a plurality of R peaks from the plurality of peaks; and
deriving the HR of the subject from the periodicity of the plurality of R peaks.

In one example, of a method for determining heart rate (HR) of a subject from noisy Electrocardiogram (ECG) data, filtering the ECG data further comprises filtering the ECG data with a low pass filter.

In one example of a method for determining heart rate (HR) of a subject from noisy Electrocardiogram (ECG) data, filtering the ECG data further comprises filtering the ECG data with a band pass filter.

In one example of a method for determining heart rate (HR) of a subject from noisy Electrocardiogram (ECG) data, filtering the ECG data further comprises filtering the ECG data with a low pass filter and a band pass filter.

In one example of a method for determining heart rate (HR) of a subject from noisy Electrocardiogram (ECG) data, transforming includes a wavelet transform function.

In one example of a method for determining heart rate (HR) of a subject from noisy Electrocardiogram (ECG) data, the wavelet transform is a stationary wavelet transform.

In one example of a method for determining heart rate (HR) of a subject from noisy Electrocardiogram (ECG) data, the wavelet transform is a discrete wavelet transform.

What is claimed is:

1. A device for determining heart rate (HR) of a subject from noisy Electrocardiogram (ECG) data, the device comprising circuitry configured to:
filter incoming ECG data to generate filtered ECG data;
transform, using a function, the filtered ECG data to a time-frequency domain to generate time-frequency data;
divide the time-frequency data to form a plurality of time-frequency data subwindows;
de-noise the time-frequency data to generate de-noised time-frequency data, wherein a dynamic threshold function is applied to each of the time-frequency data subwindows to generate the de-noised time-frequency data;
transform, using an inverse function, the de-noised time-frequency data to a time domain to generate de-noised data;
identify a plurality of peaks in the de-noised data;
derive a periodicity of a plurality of R peaks from the plurality of peaks; and
derive the HR of the subject from the periodicity of the plurality of R peaks.

2. The device of claim 1, wherein filtering the ECG data further comprises filtering the ECG data with a low pass filter.

3. The device of claim 1, wherein filtering the ECG data further comprises filtering the ECG data with a band pass filter.

4. The device of claim 1, wherein filtering the ECG data further comprises filtering the ECG data with a low pass filter and a band pass filter.

5. The device of claim 1, wherein the circuitry is further configured to filter the incoming ECG data using an infinite impulse response (IIR) filter.

6. The device of claim 1, wherein the circuitry is further configured to filter the incoming ECG data using a finite impulse response (FIR) filter.

7. The device of claim 1, wherein the circuitry is further configured to filter the incoming ECG data using a filter selected from the group consisting of Savitzky-Golay filters, Elliptic filter, Chebyshev filters, Butterworth filters, Bessel filters, and combinations thereof.

8. The device of claim 1, wherein the circuitry is further configured to include an input channel to receive the incoming ECG data.

9. The device of claim 1, wherein the function includes a wavelet transform.

10. The device of claim 1, wherein in identify the plurality of peaks and deriving the periodicity of the plurality of R peaks, the circuitry is further configured to auto-correlate the de-noised data to generate auto-correlated peak data.

11. The device of claim 1, wherein in identifying the plurality of peaks, the circuitry is further configured to apply a window function to the data to generate peak data.

12. The device of claim 1, wherein the circuitry is further configured to:
generate a notification of the derived HR; and
send the notification to an output channel.

13. A system for determining heart rate (HR) of a subject from noisy Electrocardiogram (ECG) data, comprising:

a usable object configured for physically interactive use by a subject;

at least two electrodes coupled to the usable object and positioned to facilitate ECG data recording from the subject;

circuitry including an input channel coupled to the at least two electrodes, the circuitry being configured to:

filter incoming ECG data to generate filtered ECG data;

transform, using a function, the filtered ECG data to a time-frequency domain to generate time-frequency data;

divide the time-frequency data to form a plurality of time-frequency data subwindows;

de-noise the time-frequency data to generate de-noised time-frequency data wherein a dynamic threshold function is applied to each of the time-frequency data subwindows to generate the de-noised time-frequency data;

transform, using an inverse function, the de-noised time-frequency data to a time domain to generate de-noised data;

identify a plurality of peaks in the de-noised data;

derive a periodicity of a plurality of R peaks from the plurality of peaks; and derive the HR of the subject from the periodicity of the plurality of R peaks.

14. The system of claim 13, wherein filtering the ECG data further comprises filtering the ECG data with a low pass filter.

15. The system of claim 13, wherein filtering the ECG data further comprises filtering the ECG data with a band pass filter.

16. The system of claim 13, wherein filtering the ECG data further comprises filtering the ECG data with a low pass filter and a band pass filter.

17. The system of claim 13, wherein the circuitry is further configured to filter the incoming ECG data using an infinite impulse response (IIR) filter.

18. The system of claim 13, wherein the circuitry is further configured to filter the incoming ECG data using a finite impulse response (FIR) filter.

19. The system of claim 13, wherein the circuitry is further configured to filter the incoming ECG data using a filter selected from the group consisting of Savitzky-Golay filters, Elliptic filter, Chebyshev filters, Butterworth filters, Bessel filters, and combinations thereof.

20. The system of claim 13, wherein the circuitry is further configured to include an input channel to receive the incoming ECG data.

21. The system of claim 13, wherein the function includes a wavelet transform.

22. The system of claim 13, wherein in identify the plurality of peaks and deriving the periodicity of the plurality of R peaks, the circuitry is further configured to auto-correlate the de-noised data to generate auto-correlated peak data.

23. The system of claim 13, wherein in identifying the plurality of peaks, the circuitry is further configured to apply a window function to the data to generate peak data.

24. The system of claim 13, wherein the circuitry is further configured to:

generate a notification of the derived HR; and send the notification to an output channel.

25. A method for determining heart rate (HR) of a subject from noisy Electrocardiogram (ECG) data, comprising:

filtering incoming ECG data to generate filtered ECG data;

transforming, using a function, the filtered ECG data to a time-frequency domain to generate time-frequency data;

dividing the time-frequency data to form a plurality of time-frequency data subwindows;

de-noising the time-frequency data to generate de-noised time-frequency data, wherein a dynamic threshold function is applied to each of the time-frequency data subwindows to generate the de-noised time-frequency data;

transforming, using an inverse function, the de-noised time-frequency data to a time domain to generate de-noised data;

identifying a plurality of peaks in the de-noised data;

deriving a periodicity of a plurality of R peaks from the plurality of peaks; and deriving the HR of the subject from the periodicity of the plurality of R peaks.

26. The method of claim 25, wherein filtering the ECG data further comprises filtering the ECG data with a low pass filter.

27. The method of claim 25, wherein filtering the ECG data further comprises filtering the ECG data with a band pass filter.

28. The method of claim 25, wherein transforming includes a wavelet transform function.

29. The method of claim 25, wherein the wavelet transform is a stationary wavelet transform.

30. The method of claim 25, wherein the wavelet transform is a discrete wavelet transform.

* * * * *